US008241352B2

(12) United States Patent
Young et al.

(10) Patent No.: US 8,241,352 B2
(45) Date of Patent: Aug. 14, 2012

(54) ADJUSTABLE WEIGHTED EYELID CLOSURE DEVICES AND METHODS

(75) Inventors: Allen Young, Encinitas, CA (US); John Blackmore, Redwood City, CA (US)

(73) Assignee: Aulode LLC., Woodside, CA (US)

( * ) Notice: Subject to any disclaimer, the term of this patent is extended or adjusted under 35 U.S.C. 154(b) by 131 days.

(21) Appl. No.: 12/860,831

(22) Filed: Aug. 20, 2010

(65) Prior Publication Data

US 2012/0046745 A1 Feb. 23, 2012

(51) Int. Cl.
*A61F 2/14* (2006.01)

(52) U.S. Cl. .......................................... 623/4.1; 128/898

(58) Field of Classification Search ..................... 623/4.1
See application file for complete search history.

(56) References Cited

U.S. PATENT DOCUMENTS

| 5,542,437 | A  | 8/1996  | Blackmore et al. |
| 5,830,233 | A  | 11/1998 | Suson et al.     |
| 6,206,906 | B1 | 3/2001  | Suson et al.     |
| 6,309,418 | B1 | 10/2001 | Jobe             |
| 6,482,428 | B1 | 11/2002 | Li et al.        |
| 7,108,718 | B1 | 9/2006  | Li et al.        |

FOREIGN PATENT DOCUMENTS

RU        2395258 C1 * 7/2010

* cited by examiner

*Primary Examiner* — Corrine M McDermott
*Assistant Examiner* — Randy Shay
(74) *Attorney, Agent, or Firm* — Fliesler Meyer LLP

(57) ABSTRACT

Provided herein are embodiments of a weighted eyelid closure device for use in treating lagophthalmos. In accordance with an embodiment, the device can be implanted by an oculoplastic surgeon into a patient's eyelid, to treat lagophthalmos. The device's weight can then be adjusted later by the surgeon, if necessary, without requiring removal of the entire device. For example, if it is discovered that an implanted device is too heavy or too light after it has been implanted within the patient's eyelid, the load of the device can be adjusted by modifying the previous load. Alternatively, a new load having the desired weight can be implanted.

16 Claims, 8 Drawing Sheets

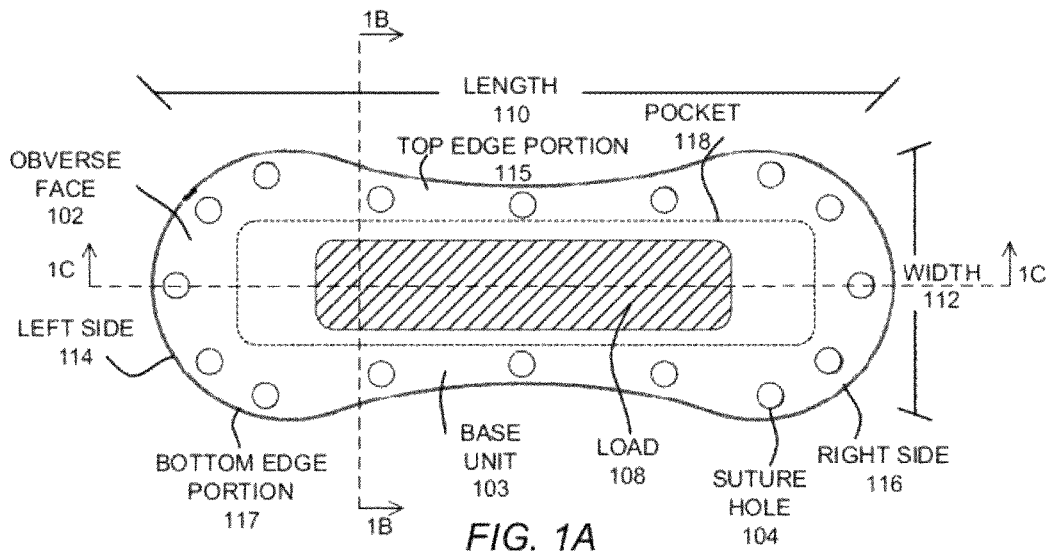
FIG. 1A
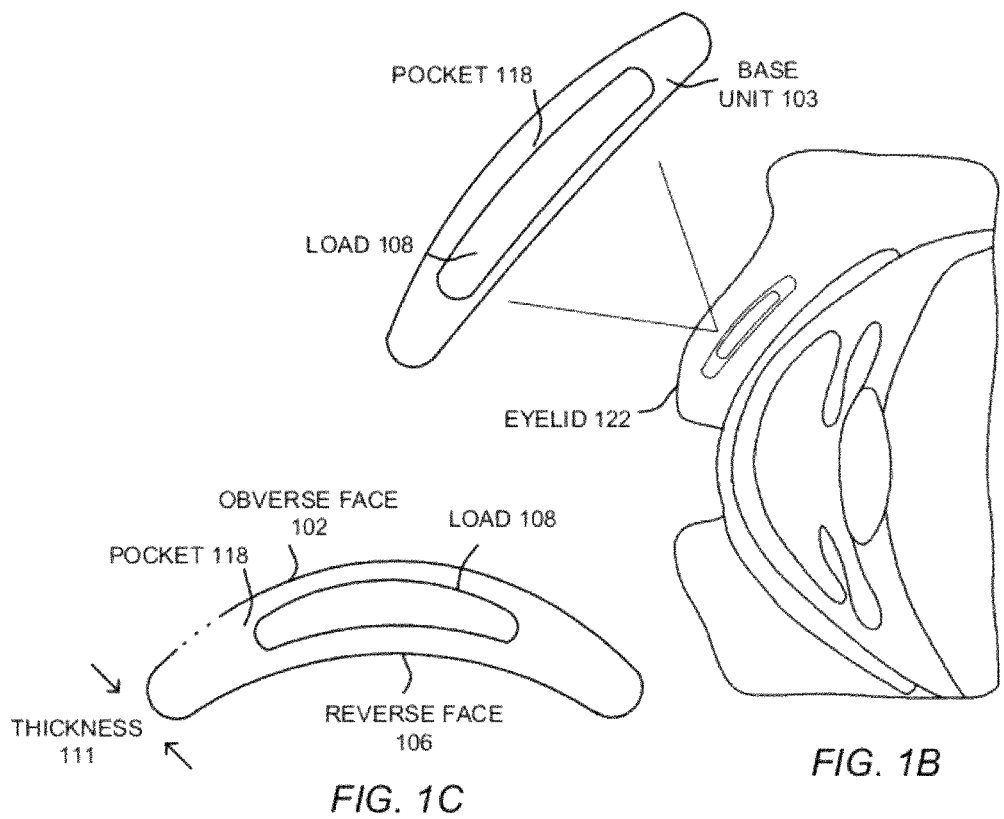
FIG. 1B
FIG. 1C

ADJUSTABLE WEIGHTED EYELID CLOSURE DEVICES AND METHODS

FIELD OF INVENTION

Embodiments of the present invention are generally related to the treatment of lagophthalmos, and are particularly related to an adjustable weighted eyelid closure device for use in improving eyelid closure.

BACKGROUND

Proper closure and blinking of the eyelids is essential for normal ocular health and functionality. This is because closing the eyes covers the eye with a thin layer of tear fluid, promoting a moist environment necessary for the cells of the exterior part of the eye. Additionally, the tears flush out foreign bodies. With incomplete eyelid closure, the eye is constantly exposed to the drying effects of outside air, as well as to dust particles and debris.

Some individuals suffer from lagopthalmos, which is the inability to close, or poor closure, of the upper eyelid. If eyelid closure is impaired, the eye can suffer abrasions and infections. The condition also can lead to corneal drying and ulceration. Thus, a critical consideration in the treatment of lagopthalmos is the protection of the eye.

Lagopthalmos can result from paralysis of the facial nerve which controls eyelid function. This paralysis can be permanent or transitory. It can also be an indirect consequence of the surgical removal of certain types of tumors in close proximity to the facial nerve control eyelid function, such as eyelid closure. Lagopthalmos can also result from other cosmetic procedures such as when a cosmetic/plastic surgeon performs an upper blepharoplasty, which is an operation performed to remove excessive skin overlying the upper eyelid that often occurs with aging. If excessive skin is removed, lagopthalmos can result. Nocturnal lagopthalmos also affects some people—a person diagnosed with nocturnal lagopthalmos is unable to close their eyelids completely when they sleep, leaving the eyes exposed to more dust and debris during the overnight hours.

Weighted eyelid implants have been used in the surgical treatment of lagopthalmos. For example, U.S. Pat. Nos. 7,108,718; 6,482,428 and 5,542,437 describe the use of weighted eyelid implants. When implanting the weight in the patient's eyelid, a surgeon makes an incision on the surface of the upper eyelid above the lashes. A small pocket is created in which the device is inserted, and the device is held in position inside this pocket with small sutures. Additional sutures are then used to reclose the incision. When the eyelids' levator muscle is relaxed, the upper eyelid is lowered by the force of gravity, substantially closing the eyelid.

Weighted eyelid implants are traditionally made of gold, making them an expensive therapy, particularly if the implants need to be replaced. In some instances the implanted weight is found to be too heavy or too light after it has been implanted within the eyelid, which can be a result of an improved or worsening of the patient's condition. Typically, in order to revise the procedure, an oculoplastic surgeon has to make an incision on the surface of the upper eyelid to remove the previously implanted weight from the suture attachment inside the eyelid, and then replace it with a new weight (of higher or lower weight) by suturing the new weight to the patient's eyelid. Additional sutures are then used to reclose the incision and the patient has to undergo the healing process again. Alternatively, a patient's ability to close their eyelid may improve, and thus require less weighted assistance to close their eyelid. Again the patient would have to undergo substantial trauma to the eyelid to remove the previously implanted weight, and replace it with an appropriate weight.

SUMMARY

Described herein are embodiments of a weighted eyelid closure device for use in treating lagopthalmos. In accordance with an embodiment, the device can be implanted by an oculoplastic surgeon into a patient's eyelid, to treat lagopthalmos. The device's weight can then be adjusted later by the surgeon, if necessary, without requiring removal of the entire device. For example, if it is discovered that an implanted device is too heavy or too light after it has been implanted within the patient's eyelid, the load of the device can be adjusted by modifying the previous load. Alternatively, a new load having the desired weight can be implanted.

In certain embodiments, the device includes a pocket capable of receiving a plurality of different loads, each load having a different weight. In an embodiment, to achieve a weight of the device which provides optimal eyelid closure, loads of different weights are formed of a size and shape that can slide into, or subsequently be removed from the pocket until a desired weight is achieved. Alternatively, a load in the form of a liquid can be injected into, or extracted from, the pocket until a desired weight of the device is achieved.

In accordance with an embodiment, the load can be modified, e.g., by adding or removing load material from the device; adding, removing, or exchanging cover plates, or other techniques to adjust the load.

In accordance with further embodiments, the weighted eyelid closure device includes an outer layer formed in an elongated concave shape, and having obverse and reverse faces, and edges associated therewith, and an inner core as part of the outer layer, said inner core separated into a plurality of sections. The outer layer is sized so that it can be implanted within the interior of a patient's eyelid, and the concave shape approximately matches that of the eyelid or eye, while the plurality of sections of the inner core can be arranged according to atomic weight. Additionally, in accordance with an embodiment, a section of the inner core referred to herein as a control disc, can be used to control the weight of the device. For example, to reduce the weight of the device, sections of the control disc can be shaved off, thus reducing the total weight of the weighted eyelid closure device. Alternatively, in an embodiment, the control disc can be provided in sections, each section having a weight and the ability to be removed, thereby affecting the total weight of the device.

In an embodiment, the inner core is separated into a plurality of sections, each section separated by a distance. The plurality of sections, when taken together, create a shape similar to the outer layer. The shape and the separating of the inner core into such sections provides for a device with a flexible body and edges, which can minimize patient discomfort by allowing the device to better conform to the natural contour of the patient's eye.

BRIEF DESCRIPTION OF THE DRAWINGS

FIG. 1 (FIGS. 1A-1C) shows an exemplary weighted eyelid closure device in accordance with an embodiment.

DETAILED DESCRIPTION

Figure 2:
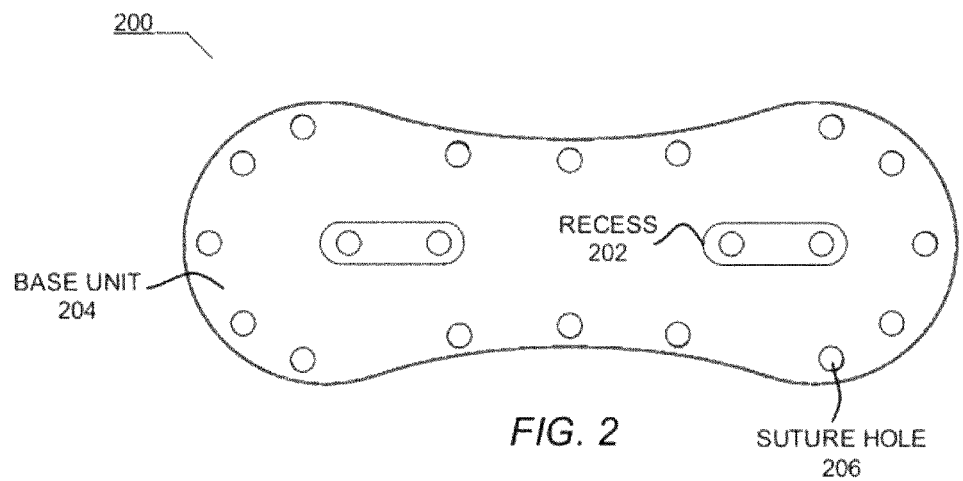
FIG. 2 shows an exemplary weighted eyelid closure device in accordance with an alternate embodiment.

As described above, a weighted eyelid closure device can be used to treat lagophthalmos. In accordance with an embodiment, the device can be implanted by an oculoplastic surgeon into a patient's eyelid, to treat lagophthalmos. The device's weight can be adjusted later by the surgeon, if necessary, without requiring removal of the entire device. For example, if it is discovered that an implanted device is too heavy or too light after it has been implanted within the patient's eyelid, the load of the device can be adjusted by modifying the previous load. Alternatively, a new load having the desired weight can be implanted.

Weighted eyelid implants are traditionally made of gold, making them an expensive therapy, particularly if the implants need to be replaced. In some instances the implanted weight is found to be too heavy or too light after it has been implanted within the eyelid, which can be a result of an improved or worsening of the patient's condition. Typically, in order to revise the procedure, an oculoplastic surgeon has to make an incision on the surface of the upper eyelid to remove the previously implanted weight, and replace it with a new weight (of higher or lower weight). Additional sutures are then used to reclose the incision and the patient has to undergo the healing process again. Alternatively, a patient's ability to close their eyelid may improve, and thus require less weighted assistance to close their eyelid. Again the patient would have to undergo substantial trauma to the eyelid to remove the previously implanted weight, and replace it with an appropriate weight.

In accordance with an embodiment, the weighted eyelid closure device can be implanted by the surgeon into the patient's eyelid to treat lagophthalmos. Unlike previous approaches, the device's weight can be adjusted later by the surgeon without removal of the entire device, the accompanying undoing and redoing of sutures, and trauma that would otherwise result.

FIG. 1 illustrates an example of a weighted eyelid closure device, in accordance with an embodiment, which can be implanted by an oculoplastic surgeon into a patient's eyelid, to treat lagophthalmos, and which can be later revised by the surgeon to adjust the weight, without requiring removal of the entire device.

As shown in FIG. 1A, in accordance with an embodiment, the device includes a base unit 103 that is capable of being implanted in a patient's eyelid, and is adapted to have a load added to, or removed from it, when implanted. In an embodiment the device is formed in a generally rectangular, bow-shaped, or similarly elongated tablet-like shape. Depending on the particular embodiment, the device can be either non-encapsulated, such as the various gold and other embodiments described in further detail below; or alternatively can include an encapsulating material, such as silicone or a similar hypoallergenic material, distributed over its entire surface.

Non-encapsulated devices should preferably be made of a biologically inert material, such as pure gold or pure platinum. In an embodiment, non-encapsulated devices can also be made of a mix of gold, platinum and/or tantalum. For example, tantalum powder could be added to molten gold to make weighted eyelid closure blanks from which the final device would be manufactured. Encapsulation allows for the use of a combination of materials, such as stainless steel, cobalt alloy, titanium alloy, and tungsten, which would otherwise create a bulky device if any one material was used to create the device. The encapsulating material can be made in a neutral color, such as the color of human fat tissue, or that of the patient's exterior eyelid, which improves cosmesis, particularly when otherwise unsuitably colored materials are used (such as darker colored tantalum). The encapsulating material can also be made with a degree of flexibility, which improves placement and patient comfort; and can include either a non-textured, or a textured surface to prevent or promote tissue adhesion respectively.

As further shown in FIG. 1A-1C, in accordance with an embodiment, the device is provided in one or more lengths 110, widths 112, and thicknesses 111 that can be selected appropriate to the needs of the individual patient. For example, typical lengths can be in increments between 10 mm and 15 mm, typical widths in increments between 5 mm and 10 mm, and typical thicknesses in increments between 0.5 mm and 3 mm. In accordance with an embodiment, in a therapeutic setting a plurality of different sizes (weight and length) of the device can be provided as part of a kit, and the surgeon or a fitting specialist can select from the kit the particular size of the device most suitable for the patient's needs. In those embodiments which include colored devices, the kit can also include devices of different colors that allow the surgeon to select a color that blends best with the patient's overlying skin color.

In accordance with an embodiment, when viewed from its obverse face, each device includes an obverse face 102, and a reverse face 106; left and right edge portions 114, 116 respectively; and top and bottom edge portions 115 and 117 respectively. A plurality of suture holes 104 can be distributed around the perimeter of the device, which collectively allow the device to be sutured to the orbital septum or tarsus, placing the device securely parallel to the eyelid margin. The surgeon will be in the best position to determine which suture holes, and which types of suture, to use, depending on the patient's physiology and the particular surgery. Suture holes which are not used, but are instead left vacant, can provide useful areas for future tissue growth, which can help to stabilize the device in the patient's eyelid.

In accordance with an embodiment, the left and right edge portions can be round-shaped, and can be tapered or contoured to reduce sharp corners. This provides a measure of comfort to the patient, and since the curved profile is less noticeable than a straight profile, results in a more natural appearance and improves overall cosmesis. The top and bottom, and left and right sides can similarly be shaped and/or contoured, both to provide a measure of comfort to the patient, and also to distribute the weight of the device away from the center of the eyelid, and towards the left and right edges of the device and of the patient's eyelid, which improves function, comfort, and cosmesis.

In accordance with an embodiment, either the obverse or the reverse face of the device includes a pocket, fastener, or other means of securing a load to the device. For example, FIG. 1B illustrates a section view through line 1B-1B of FIG. 1A where, in accordance with an embodiment, the device includes a pocket 118 on the base unit's 103 obverse face that receives a load 108, which can be alternately removed or replaced to modify the total weight of the device. In accordance with an embodiment, the load can be made of a material similar to the device itself, such as gold, platinum, stainless steel, cobalt alloy, titanium alloys, or combinations thereof, and can be similarly encapsulated or non-encapsulated.

In accordance with an embodiment, the pocket is located in such a position on the device, so that when the device has been implanted within the patient's eyelid 122, and sutured therein, the surgeon can later access the load to remove and/or replace the original load with a modified load, and adjust the total weight of the device, without removing the device itself. In accordance with an embodiment, an open-ended pocket is provided on the obverse face of the device, and variable weighted loads are formed of a size and shape that they can be selected and slid into, or subsequently removed from the pocket. Depending on the particular embodiment, as described in further detail below, the load can be modified, e.g., by adding or removing load material from the device; adding, removing, or exchanging cover plates, or other techniques to adjust the load.

As described above, often with patients suffering from lagophthalmos there is a need to revise the surgical procedure due to an improvement or worsening in the patient's condition. Using the above technique, the surgeon is able to revise the surgical procedure, substantially without removal of the device and the accompanying undoing and redoing of previous sutures, and thus, trauma to the eyelid area is substantially reduced, as is the patient's healing time.

FIG. 1C illustrates a section view through line 1C-1C of FIG. 1A. In accordance with an embodiment, the device's elongated tablet-like shape is formed in an approximately concave shape, similar to a portion of a sphere, and so that the curvature of the inner reverse face generally approximates the curvature of the human eye, and improves both comfort and cosmesis. In accordance with an embodiment, the radius of curvature of such concave shape can be in the range of 33.55 mm to 10 mm, although as with the other sizes and dimensions described above, these dimensions can similarly vary depending on the particular size of device chosen, and the individual patient's needs.

FIG. 2 illustrates an exemplary weighted eyelid closure device 200, in accordance with an embodiment. As shown in FIG. 2, in accordance with an embodiment, the device includes a surgical staple recess 202, which allows the device to be implanted within a patient's eyelid using surgical staples, and without the use of sutures. Additionally, the staples are recessed into channels, improving function, comfort, and cosmesis. When implanting the device in the patient's eyelid, the surgeon makes an incision on the surface of the upper eyelid above the lashes. A small pocket is created in which the device is inserted. Depending on the patient's physiology, the surgeon can use either the plurality of suture holes 206 distributed around the perimeter of the device, or the surgical staple recess to suture the device to the orbital septum or tarsus, placing the device securely parallel to the eyelid margin.

In accordance with an embodiment, the base unit 204 of the device can be formed of the encapsulating material, such as silicone or a similar hypoallergenic material. The encapsulating material can be made with a degree of flexibility, which improves placement and patient comfort; and can contain a mixture of relatively lower volume material (i.e., Higher Atomic Weight Material, HAWM) such as gold, platinum or tantalum, or a combination thereof, with a relatively higher volume material (i.e., Lower Atomic Weight Material, LAWM) such as stainless steel, cobalt alloys and titanium alloys.

In accordance with an embodiment, the device can be made to have different weights by altering the mixture of two or more materials. The process includes selecting a desired total volume, and a plurality of desired total weights. To achieve each desired total weight, while maintaining the total volume of the device substantially the same, the ratio between the first material and the second material is adjusted. For example, in accordance with an embodiment, Table 1 shows two materials, tantalum and cobalt, used to manufacture base unit 204. As illustrated therein, the desired total volume of the device remains substantially the same, while each desired total weight of 0.6, 0.8, 1.0, 1.2 and 1.4 grams is obtained by altering the ratio of tantalum to cobalt. It will be evident that the examples provided in Table 1 are provided for purposes of illustration, and that in accordance with other embodiments, other material ratios, volume and weights could be used.

TABLE 1

| MATERIAL CHARAC- TERISTIC | RATIO OF MATERIAL | | TOTAL VOLUME (cubic centimeters) | TOTAL WEIGHT (grams) |
|---|---|---|---|---|
| | Tantalum | Cobalt | | |
| VOLUME | 0 | 0.06741573 | 0.06741573 | |
| WEIGHT | 0 | 0.6 | | 0.6 |
| VOLUME | 0.006004563 | 0.078651685 | 0.084656249 | |
| WEIGHT | 0.1 | 0.7 | | 0.8 |
| VOLUME | 0.031523958 | 0.053370787 | 0.084894745 | |
| WEIGHT | 0.525 | 0.475 | | 1 |
| VOLUME | 0.057343581 | 0.02752809 | 0.084871671 | |
| WEIGHT | 0.955 | 0.245 | | 1.2 |
| VOLUME | 0.084063889 | 0 | 0.084063889 | |
| WEIGHT | 1.4 | 0 | | 1.4 |

When the device is implanted within a patient's eyelid by a surgeon, the base unit of the device takes on a spherical-shape more closely matching the natural contour of a patient's eye. Devices having a spherical shape are less noticeable since the device lays flush with the patient's eye, which improves function, comfort, and cosmesis.

In accordance with an embodiment, the base unit of the device can encase tantalum, and be of a color similar to human flesh or fat tissue so as to blend in with the patient's natural eyelid color. This allows the treated eyelid to outwardly resemble that of an untreated eyelid. Traditional implants are fabricated using gold. A weighted eyelid closure device fabricated using tantalum, or a mixture of alloys, and encased in a material the color or flesh or fat, can be more economical to manufacture when compared to weighted eyelid devices fabricated from gold.

Figure 3:
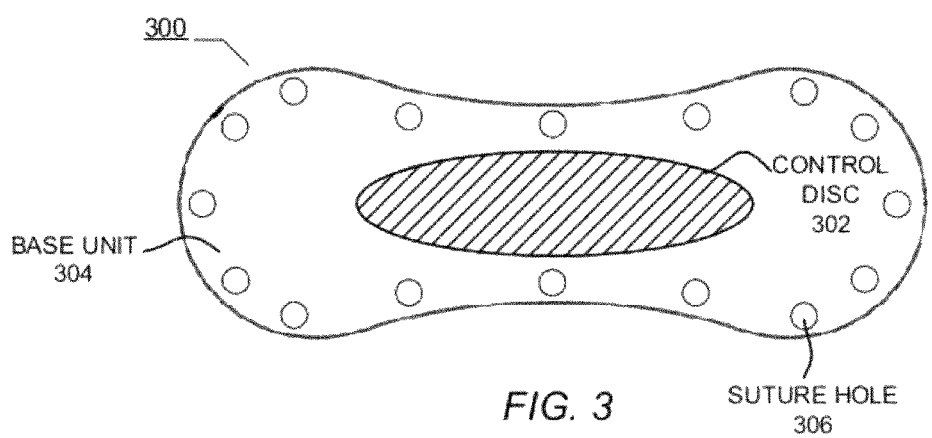
FIG. 3 shows an exemplary weighted eyelid closure device in accordance with a particular embodiment.

FIG. 3 illustrates an exemplary weighted eyelid closure device 300, in accordance with an embodiment, which includes a control disc 302 in the base unit 304 that can be used to adjust the weight of the weighted eyelid closure device.

Prior to implanting the device into the patient's eyelid, a surgeon or a fitting specialist determines the most suitable weight for the device. This can be accomplished by, for example, using a kit that includes a number of different weights. The weights are not implanted within the eyelid, but are instead temporarily affixed to the exterior of the patient's eyelid. The weights are used to determine the appropriate weight of a device required for optimum closure of the eyelid by selecting one of the weights, temporarily affixing the weight to the exterior of the eyelid, and observing the position of the eyelid as the patient performs normal eye movement, e.g., looking up, down and blinking. The weight is then removed and, if necessary, a weight having a higher or lower weight is temporarily secured to the eyelid for testing. In accordance with an embodiment, once the appropriate weight to achieve optimum eyelid closure in the patient has been determined, the surgeon or fitting specialist can have the device's weight adjusted, for example by, trimming the control disc. The surgeon or fitting specialist has the option of either trimming the control disc themselves using an appropriate trimming tool to achieve the appropriate weight needed to optimally close the patient's eyelid, or can send the device to a specialist who can trim the control disc to the appropriate weight. Alternatively, the surgeon or fitting specialist can order an already trimmed device directly from a device manufacturer.

Upon determining the appropriate total weight of the device, the surgeon will implant the device in the patient's eyelid. When implanting the device in the patient's eyelid, the surgeon makes an incision on the surface of the upper eyelid above the lashes. A small pocket is created in which the device is inserted. The surgeon uses the plurality of suture holes 306 distributed around the perimeter of the base unit to suture the device to the orbital septum or tarsus, placing the device securely parallel to the eyelid margin, and closes the incision with addition sutures.

Figure 4:
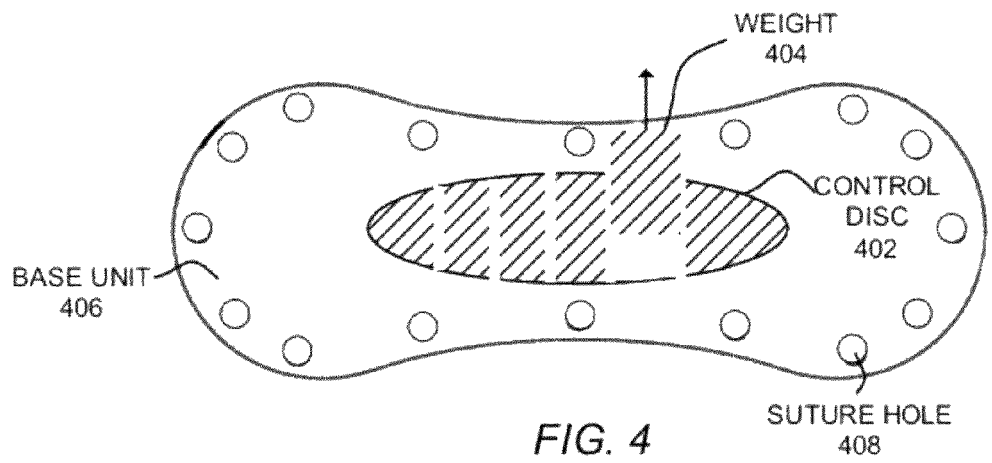
FIG. 4 shows an exemplary weighted eyelid closure device in accordance with an alternate embodiment.

Additionally, as shown in FIG. 4, in accordance with an embodiment, a weighted eyelid closure device includes a control disc 402 in the base unit 406, which can be manufactured as a mix of the HAWM or LAWM. The control disc is provided in sections, each section having a weight 404 (e.g., in one embodiment 0.3 grams), and the sections are designed to break away from the control disc when pressure is exerted on them. To modify the total weight of the device, the surgeon removes one or more of the sections.

In an embodiment, the control disc including removable sections, is located in such a position on the device, that when the device has been implanted within the patient's eyelid, and sutured therein using suture holes 408 distributed around the perimeter of base unit 406, the surgeon can later access the control disc to remove one or more sections to adjust the total weight of the device, without removing the entire device. In an embodiment, the device can be offered in various weights, with the ability to adjust the device's weight by removing sections of the control disc. In accordance with an embodiment, a kit can be provided which includes various weighted eyelid closure devices, each device having a control disc, and each device being of a different weight. For example, the kit can include one or more devices having default weights, such as, 0.2, 0.3 and 0.4 grams, and a control disc (having for example, five section) adding an additional weight. In an embodiment, each section of the control disc can weigh 0.3 grams. Alternatively, each section can have a different weight, e.g., the five sections can respectively weigh 0.2, 0.3, 0.4, 0.5 and 0.6 grams each. The surgeon can then select the appropriate device having a desired default weight, and adjust the device's weight using the included weighted sections to the weight that optimally closes the patient's eyelid. In those embodiments which include colored devices, the kit can also include devices of different colors that allow the surgeon to select a color that blends best with the patient's skin color.

In accordance with an embodiment, once a surgeon determines the appropriate weight to achieve optimum eyelid closure, for example using the method described in FIG. 3, the surgeon implants the device in the patient's eyelid. When implanting the device in the patient's eyelid, the surgeon makes an incision on the surface of the upper eyelid above the lashes. A small pocket is created in which the device is inserted. The surgeon uses the plurality of suture holes distributed around the perimeter of the base unit to suture the device to the orbital septum or tarsus, placing the device securely parallel to the eyelid margin, and closes the incision with addition sutures. If a patient's condition later changes such that less weight is required to maintain optimum eyelid closure, the surgeon can easily adjust the weight of the device by making an incision in the patient's eyelid where the implant is located, remove sections of the control disc, and then reclose the incision.

Figure 5A:
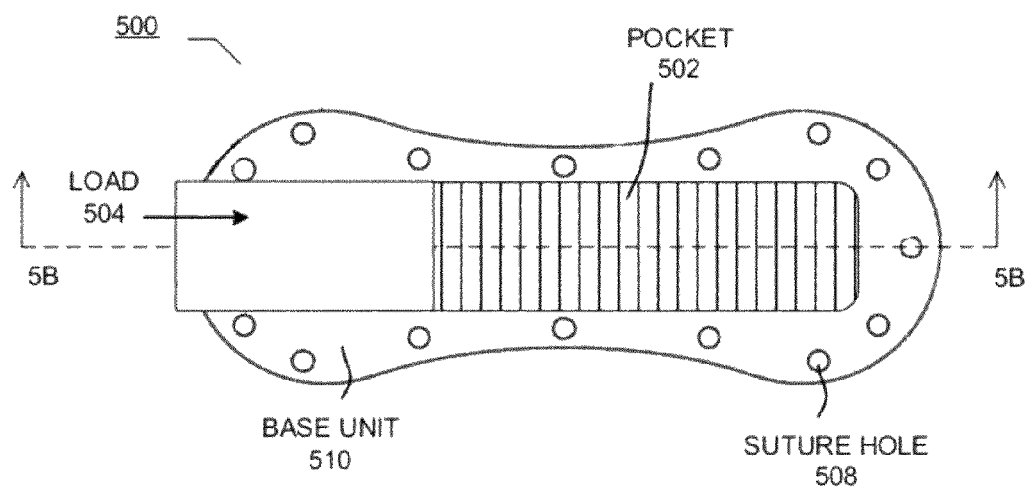
FIG. 5 (FIGS. 5A-5B) shows an exemplary weighted eyelid closure device in accordance with an alternate embodiment.
Figure 5B:
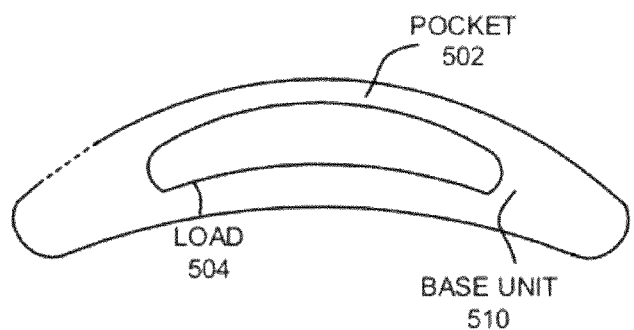

FIGS. 5A and 5B illustrate a weighted eyelid closure device 500, in accordance with an embodiment, which can be implanted by a surgeon into a patient's eyelid, to treat lagophthalmos, and which can be later revised by the surgeon to adjust the weight, without requiring removal of the entire device.

As shown in FIG. 5A, in accordance with an embodiment, the device includes a pocket 502 on the base unit 510. The pocket is configured to receive a load 504, which can be alternately removed or replaced, to modify the total weight of the device. In accordance with an embodiment, the pocket is located in such a position on the base unit, so that when the base unit has been implanted within the patient's eyelid, and sutured therein using the plurality of suture holes 508 distributed around the perimeter of the base unit, the surgeon can later access the load to remove and/or replace the original load with a modified load, and adjust the total weight of the device, without removing the device itself. In accordance with an embodiment, an open-ended pocket is provided on the obverse face of the base unit, and variable weighted loads are formed of a size and shape that they can be slide into, or subsequently removed the pocket. For example, in accordance with an embodiment, the load can be inserted into the pocket from the left side. Although in FIG. 5A, the opening of the pocket is shown on the left side of the base unit, the opening is not limited thereto. For example, in accordance with various embodiments, the opening of the pocket can be located on any of the four sides of the device, or for example, the opening to the pocket can be a slit in the middle of the base unit. Before implanting the base unit in the patient's eyelid, the surgeon slides the load into the pocket until the load is substantially enclosed therein, and is held in by the pocket.

In accordance with an embodiment, a plurality of loads, each having a different weight can be provided in a kit to the surgeon. A surgeon can adjust the weight of the device by removing and/or replacing the load in the pocket. For example, FIG. 5B illustrates a section view through line 5B-5B of FIG. 5A which, in accordance with an embodiment, illustrates the load 506 being inserted into the pocket 502 from the left of base unit 510. Thus, in accordance with an embodiment, once the desired weight for device has been determined (e.g., as described in FIG. 3), the appropriate weight can be inserted into the pocket to provide optimum eyelid closure, and the surgeon can implant the device into the eyelid of the patient. If a patient's condition changes such that more or less weight is required to optimally close the patient's eyelid, the surgeon can revise the procedure to adjust the total weight of the device. To revise the procedure, the surgeon makes an incision in the patient's eyelid where the implant is located, and adjusts the total weight of the device by removing and/or replacing the load in the pocket. The surgeon then closes the incision.

Figure 6:
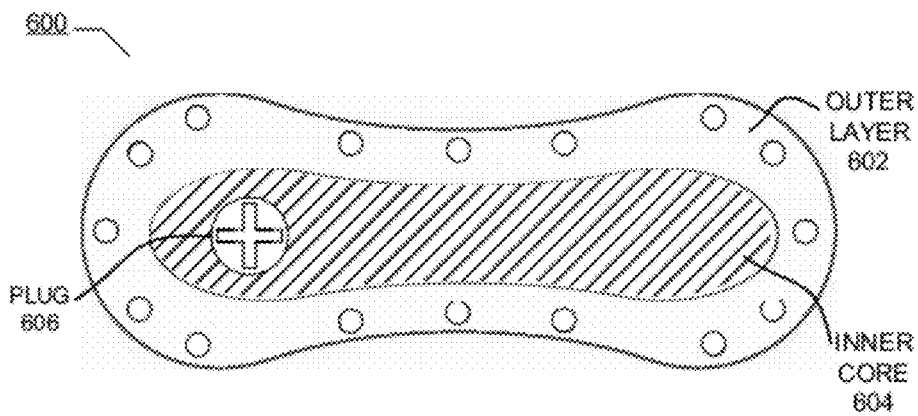
FIG. 6 shows an exemplary weighted eyelid closure device in accordance with an alternate embodiment.

FIG. 6 illustrates an exemplary weighted eyelid closure device 600, in accordance with an embodiment, the device's elongated tablet-like shape is formed in an approximately concave shape, similar to a portion of a sphere, and so that the curvature of the inner reverse face generally approximates the curvature of the human eye, and improves both comfort and cosmesis.

As shown in FIG. 6, in accordance with an embodiment, the device includes an outer layer 602 formed in an approximately concave shape, and an inner core 604 having a radius of curvature substantially conforming to a curvature of the human eye. In accordance with a particular example, the radius of curvature of such concave shape can be in the range of 11.5 mm to 13.5 mm, although as with other sizes and dimensions described above, these dimensions can similarly vary depending on the individual patient's needs.

In an embodiment, the inner core can be solid or house a repository that can be filled with a suitable load (e.g., a tantalum powder/gel) to adjust the weight of the device. A surgeon can fill the repository by removing a plug 606 that covers a channel leading to the repository, and can use an appropriate device (e.g., syringe) to fill the repository to the desired weight required to provide optimal eyelid closure. When implanting the device in the patient's eyelid, the surgeon makes an incision on the surface of the upper eyelid above the lashes. A small pocket is created in which the device is inserted. The surgeon uses the plurality of suture holes distributed around the perimeter of the device to suture the device to the orbital septum or tarsus, placing the device securely parallel to the eyelid margin, and closes the incision with addition sutures. If a patient's condition changes such that more or less weight is required to optimally close the patient's eyelid, the surgeon can adjust the weight of the device by making an incision in the patient's eyelid where the implant is located, removing the plug and adjusting the weight of the device by adding or extracting the appropriate load from the repository using a syringe or other appropriate device, and upon securing the plug in place, reclose the incision using sutures.

In accordance with another embodiment, the inner core can be a self-healing elastomer, such as silicone rubber, and be filled by piercing the inner core and injecting a load into the repository from outside the patient's eyelid. Advantageously, the surgeon does not have to make an incision in the patient's eyelid where the implant is located to remove the plug to fill or extract the appropriate load from the repository, and instead, the surgeon either injects or extracts the appropriate load from the device from the outside of the patient's eyelid to adjust the device's weight. In an embodiment, once the desired weight for the device has been determined, the repository can be filled with the appropriate weight to provide optimum eyelid closure and then implanted within the eyelid of the patient. If there is a need to revise the surgical procedure due to an improvement or worsening in the patient's aliment, the surgeon is able to revise the surgical procedure, without removal of the device and the accompanying undoing and redoing of previous sutures to suture close the eyelid, and can either inject or extract the appropriate load to adjust the weight of the device.

Figure 7:
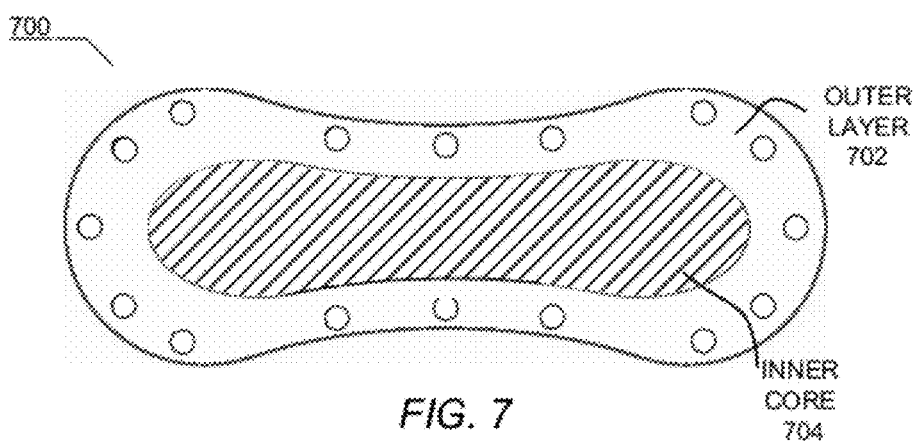
FIG. 7 shows an exemplary weighted eyelid closure device in accordance with an alternate embodiment.

As illustrated in FIG. 7, in accordance with an embodiment, the weighted eyelid closure device 700 includes an outer layer 702 and an inner core 704. In an embodiment, the outer layer and the inner core can be an alloy mix, for example a tantalum and cobalt mix. Alternatively, the outer layer and the inner core can be materials which are bonded together. For example, the outer layer can be a LAWM such as, e.g., stainless steel, cobalt alloys and titanium alloys, while the inner core can be a HAWM such as, e.g., gold, platinum or tantalum, or a combination thereof. The shape and flexibility of the outer layer and the inner core can minimize patient discomfort by allowing the device to better conform to the patient's eye. In an embodiment, a kit can be provided that provides various devices having different weights due to the mix of the material used. Thus, in accordance with an embodiment, once the desired weight for the device has been determined, a device having the appropriate weight to provide optimum eyelid closure can be selected and then be implanted within the patient's eyelid by making an incision in the patient's eyelid, placing the device into the eyelid, suturing the device to the patient's eyelid and suturing close the incision.

Figure 8:
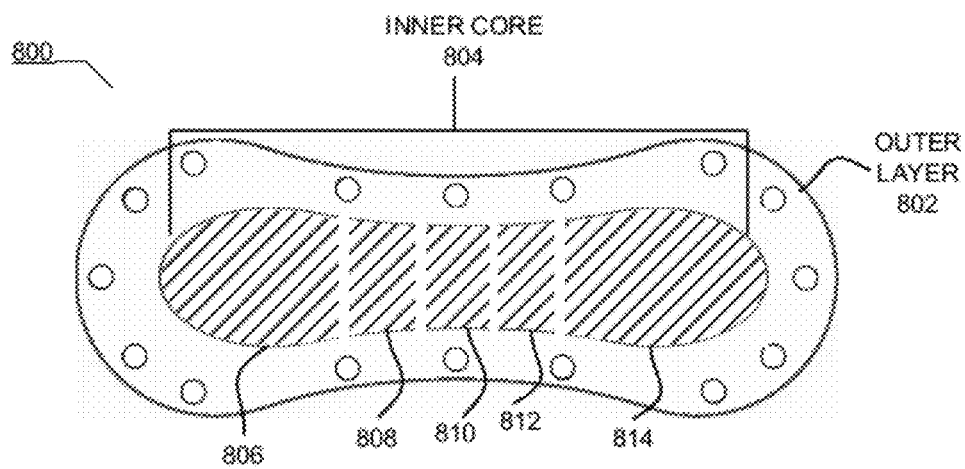
FIG. 8 shows an exemplary weighted eyelid closure device in accordance with an alternate embodiment.

In accordance with an embodiment, FIG. 8 illustrates an inner core 804 provided as a plurality of sections 806, 808, 810, 812 and 814. Although in this embodiment the inner core is provided as five separate sections, it will be appreciated that the inner core can be provided into more or less sections. The sections, when taken together, create a shape substantially similar to the outer layer. The shape and the separating of the inner core into such sections can minimize patient discomfort, by allowing the device to better conform to the natural contour of the patient's eye. In a specific embodiment, the sections can be made of different materials. In accordance with a particular example, the sections 808, 810 and 812 can be a LAWM such as, e.g., stainless steels, cobalt alloys and titanium alloys, while the sections 806 and 814 can be a HAWM such as, e.g., gold, platinum or tantalum. Placing the LAWM near the inner sections and the HAWM in the outside sections of the inner core better distributes the weight of the device across the patient's eye, which improves function, comfort, and cosmesis when implanted.

In an embodiment, a kit can be provided that includes devices having different weights due to the mix of the material used. In accordance with an embodiment, once the desired weight for the device has been determined, a device having the appropriate weight to provide optimum eyelid closure can be selected and then implanted within the patient's eyelid by making an incision in the patient's eyelid, placing the device into the eyelid, and then suturing the device to the patient's eyelid.

FIG. 9 shows an exemplary weighted eyelid closure device 900, in accordance with an embodiment, which can be later revised by a surgeon to adjust the weight, without requiring removal of the entire device.

Figure 9A:
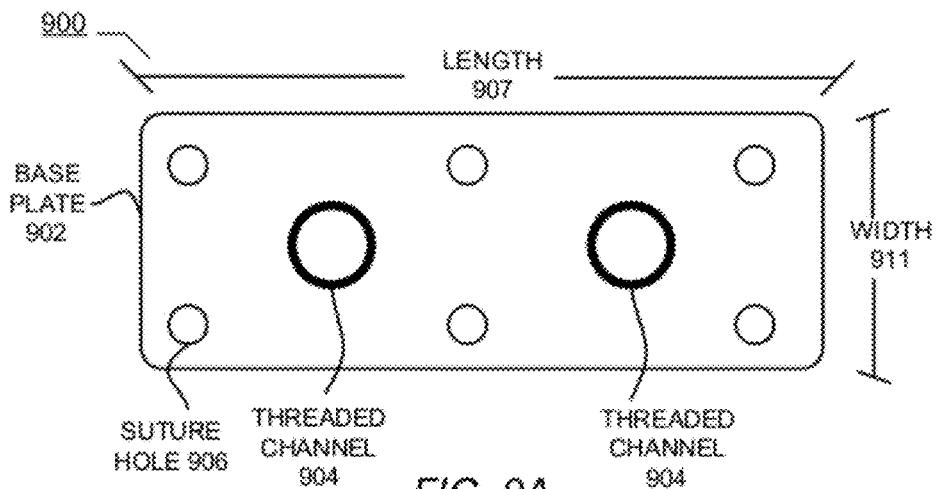
FIG. 9 (FIGS. 9A-9C) shows an exemplary weighted eyelid closure device in accordance with an alternate embodiment.

As shown in FIG. 9A, in an embodiment, a base plate 902 includes one or more threaded channels 904 and one or more suture holes 906, which collectively allow the device to be sutured within the eyelid. The surgeon will be in the best position to determine which suture holes, and which types of suture to use, depending on the patient's physiology. Suture holes which are not used, but are instead left vacant, can provide useful areas for future tissue growth, which can help stabilize the device in the patient's eyelid. In an embodiment, the base plate can be a higher volume (LAWM) material such as, e.g., cobalt, and weigh 0.6 grams, but is not limited to said material and weight. In accordance with a particular example, the device is provided in one or more lengths 907, widths 911, and thicknesses that can be selected appropriate to the needs of the individual patient. For example, typical lengths of the base plate can be in increments between 15 mm to 25 mm, typical widths in increments between 5 mm to 10 mm, and typical thicknesses in increments between 0.5 mm to 3 mm.

Figure 9B:
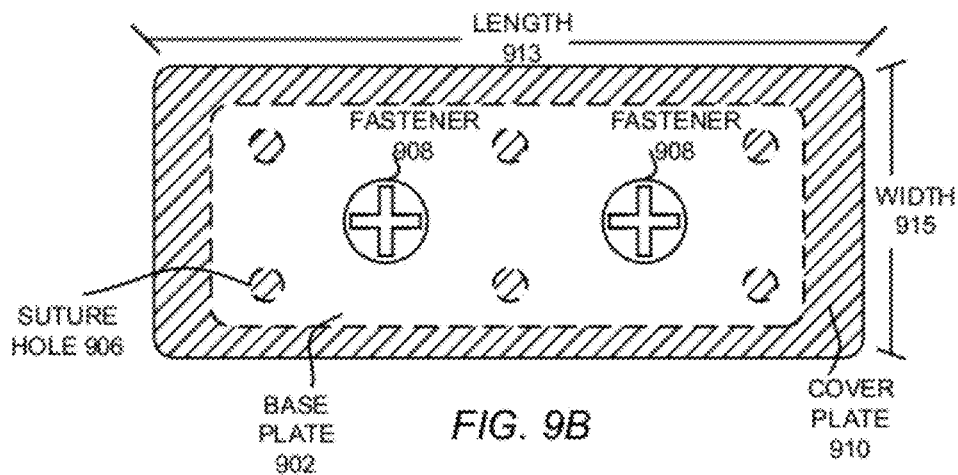
Figure 9C:
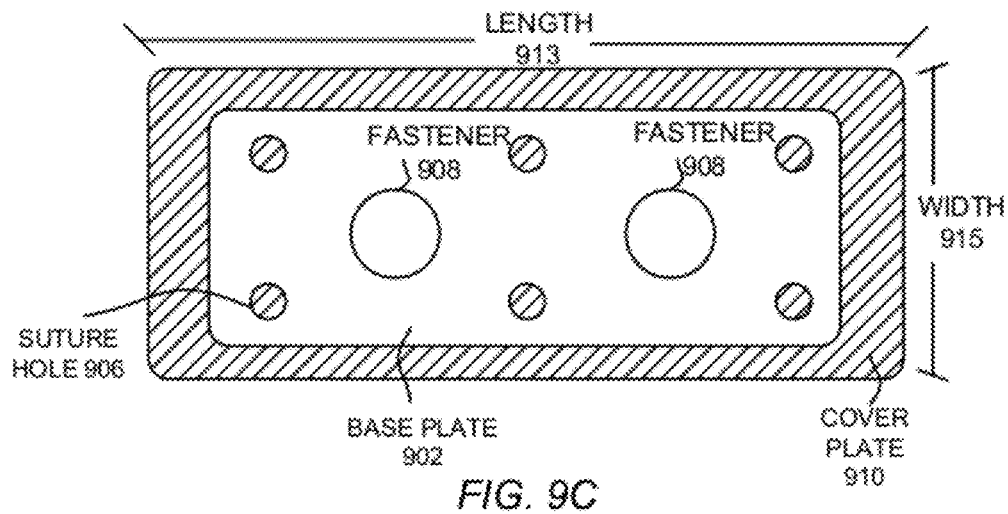
Figure 10A:
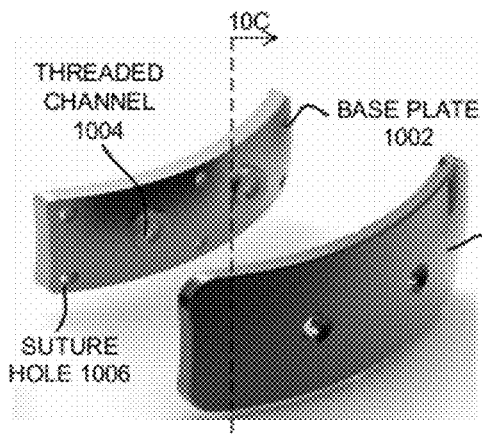
FIG. 10 (FIGS. 10A-10D) shows an exemplary weighted eyelid closure device in accordance with an alternate embodiment.
Figure 10B:
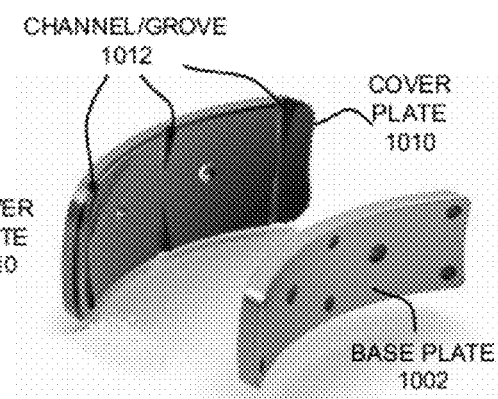
Figure 10C:
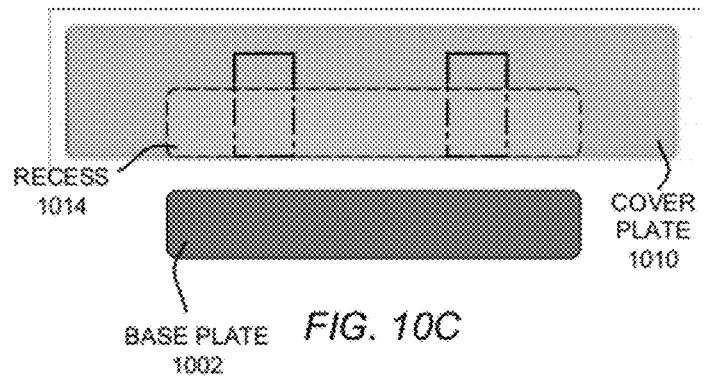
Figure 10D:
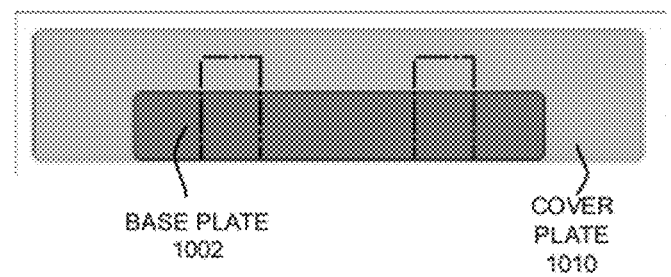

FIG. 9B illustrates a posterior view of the base plate 902 when attached to the cover plate 910, while FIG. 9C illustrates an anterior view of the base plate 902 when attached to the cover plate 910. In accordance with an embodiment, a surgeon uses one or more fasteners 908 to attach the base plate 902 to the cover plate 910, and the suture holes 906 to implant the base plate to the patient's eyelid. For example, when implanting the base plate, the surgeon makes an incision on the surface of the upper eyelid above the lashes. A small pocket is created in which the base plate is inserted. The surgeon uses the plurality of suture holes to suture the base plate to the orbital septum or tarsus, placing the device securely parallel to the eyelid margin. Once the base plate is implanted within the patient's eyelid, the surgeon aligns the cover plate with the base plate such that the threaded channels on the base plate register with recesses on the cover plate. The surgeon then aligns the fastener 908 with the threaded channel, which is used to secure the cover plate to the base plate, and uses additional sutures to reclose the incision.

In accordance with an embodiment, once the desired weight for the device has been determined (as described in FIG. 3), the base plate can be implanted within the patient's eyelid, at or near the orbital septum or tarsus, placing the device securely parallel to the eyelid margin. An appropriate cover plate can then be attached to the base plate to provide the appropriate weight to provide the desired eyelid closure. If a patient's condition changes such that more or less weight is required to optimally close the patient's eyelid, the surgeon can adjust the weight of the device by making an incision in the patient's eyelid where the implant is located, remove the existing cover plate and replace it with a cover plate having a desired weight that optimally closes the patient's eyelid, and then suture close the incision.

In an embodiment, the cover plate can be a HAWM such as tantalum, and weigh 0.2 grams, but is not limited to said material and weight. In accordance with a particular example, the cover plate is provided in one or more lengths 913, widths 915, and thicknesses that can be selected appropriate to the needs of the individual patient. For example, typical lengths can be in increments between 19 mm to 30 mm, typical widths in increments between 7 mm to 15 mm, and typical thicknesses in increments between 0.5 mm to 3 mm, but is not limited thereto.

FIG. 10 shows an additional view of the weighted eyelid closure device, in accordance with an embodiment. As illustrated in FIG. 10A, in accordance with an embodiment, the threaded channels 1004 can be from, but are not limited thereto, about 2 mm wide with a 1 mm hole and a 2 mm depth. As described above in FIG. 9, suture holes (e.g., 1006) can be distributed around the perimeter of the device, which collectively allow the device to be sutured within the eyelid. In an embodiment, the base plate 1002 is implanted within a patient's eyelid by a surgeon by making an incision in the patient's eyelid, placing the base plate into the eyelid, and suturing the base plate to the patient's eyelid by inserting sutures through one or more of the sutures holes. A surgeon then uses one or more fasteners (e.g., 908) to attach the base plate 1002 to the cover plate 1010, and additional sutures to reclose the incision. As illustrated in FIG. 10B, in accordance with an embodiment, the cover plate 1010 includes one or more recessed channels or grooves 1012, which receive the sutures used to attach the base plate 1002 to the eyelid, and when the cover plate and base plate are fastened together, they can be fastened flush to one another. For example, FIGS. 10C-10D illustrate a section view through line 10C-10C of FIG. 10A where, in accordance with an embodiment, the cover plate includes a recess 1014 to accommodate the base plate. The base plate is implanted within the patient's eyelid, and when the cover plate is attached, it completely covers the base plate, which improves function, comfort, and cosmesis.

Figure 11A:
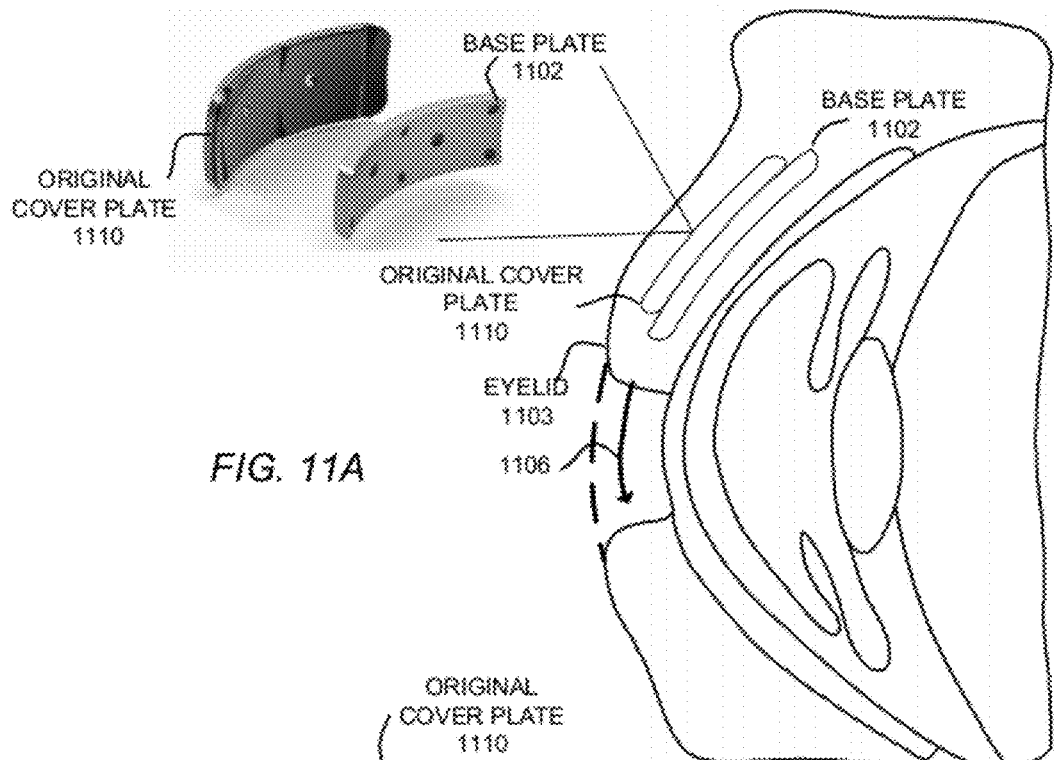
FIG. 11 (FIGS. 11A-11B) shows an illustration of the installation and use of a weighted eyelid closure device in accordance with an embodiment.

FIG. 11 shows an illustration of the installation and use of a weighted eyelid closure device, in accordance with an embodiment. As shown in FIG. 11A, in an embodiment, once the desired weight for the device has been determined (as described in FIG. 3), a base plate 1102 can be surgically implanted by a surgeon in a patient's eyelid. When implanting the base plate in the patient's eyelid, the surgeon makes an incision on the surface of the upper eyelid above the lashes. A small pocket is created in which the base plate is inserted. The surgeon uses the plurality of suture holes distributed around the perimeter of the device to suture the device to the orbital septum or tarsus, placing the device securely parallel to the eyelid margin. A cover plate, e.g., original cover plate 1110, is selected and attached to the base plate to provide the appropriate weight for optimum eyelid closure. Once the cover plate is attached to the base plate, the surgeon closes the incision with addition sutures. Although the device is shown using base plate 1102 and cover plate 1110, the embodiments described above are also suitable as alternative weighted eyelid closure devices. Upon implanting the device within the patient's eyelid, when the levator muscle is relaxed, the patient's eyelid 1103 is lowered by the force of gravity (1106), substantially closing the eyelid.

Figure 11B:
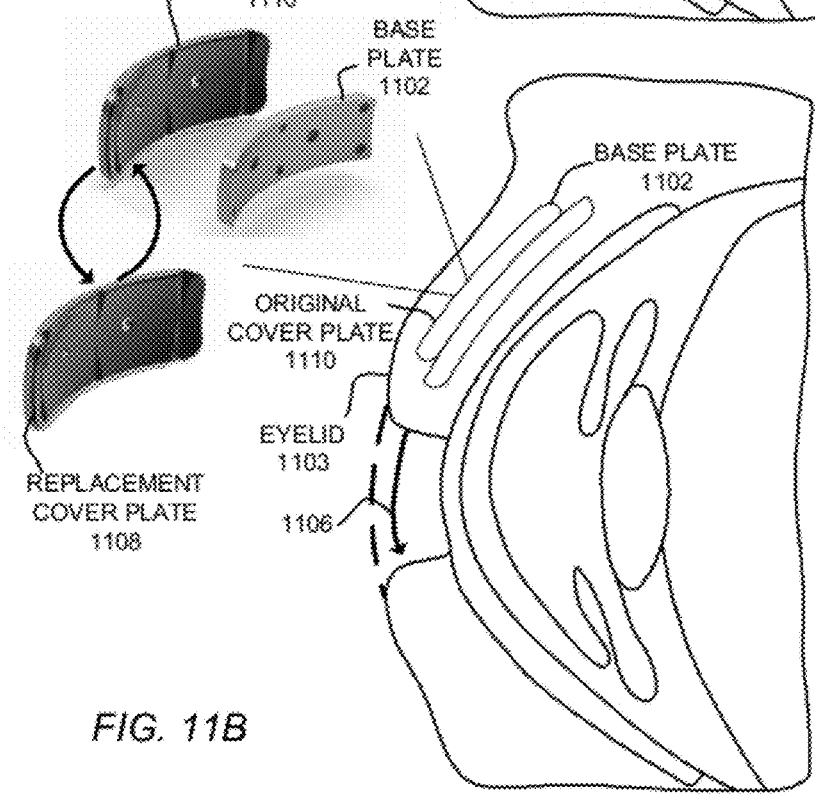

Traditionally, when the implanted weight was found to be too heavy or too light after it had been implanted within the patient's eyelid, a surgeon would have to perform a surgical procedure to remove the previously implanted weight and replace it with a new weight (of higher or lower weight). However, as shown in FIG. 11B, in accordance with an embodiment, the weight of the device can be adjusted after implanting the device in an eyelid by replacing the original cover plate 1110 with a replacement cover plate 1108 of a different weight. In performing this procedure, a surgeon makes an incision in the patient's eyelid where the implant is located, removes the original cover plate by removing the connecting fasteners (e.g., fastener 908), attaches a replacement cover plate of a different weight to the already implanted base plate, and then closes the incision. This surgical procedure advantageously allows a surgeon to later adjust the weight of the device without requiring removal of the entire device. Upon installing the replacement cover plate, the patient's eyelid 1103 is lowered by the force of gravity (1106) when the levator muscle is relaxed.

Figure 12:
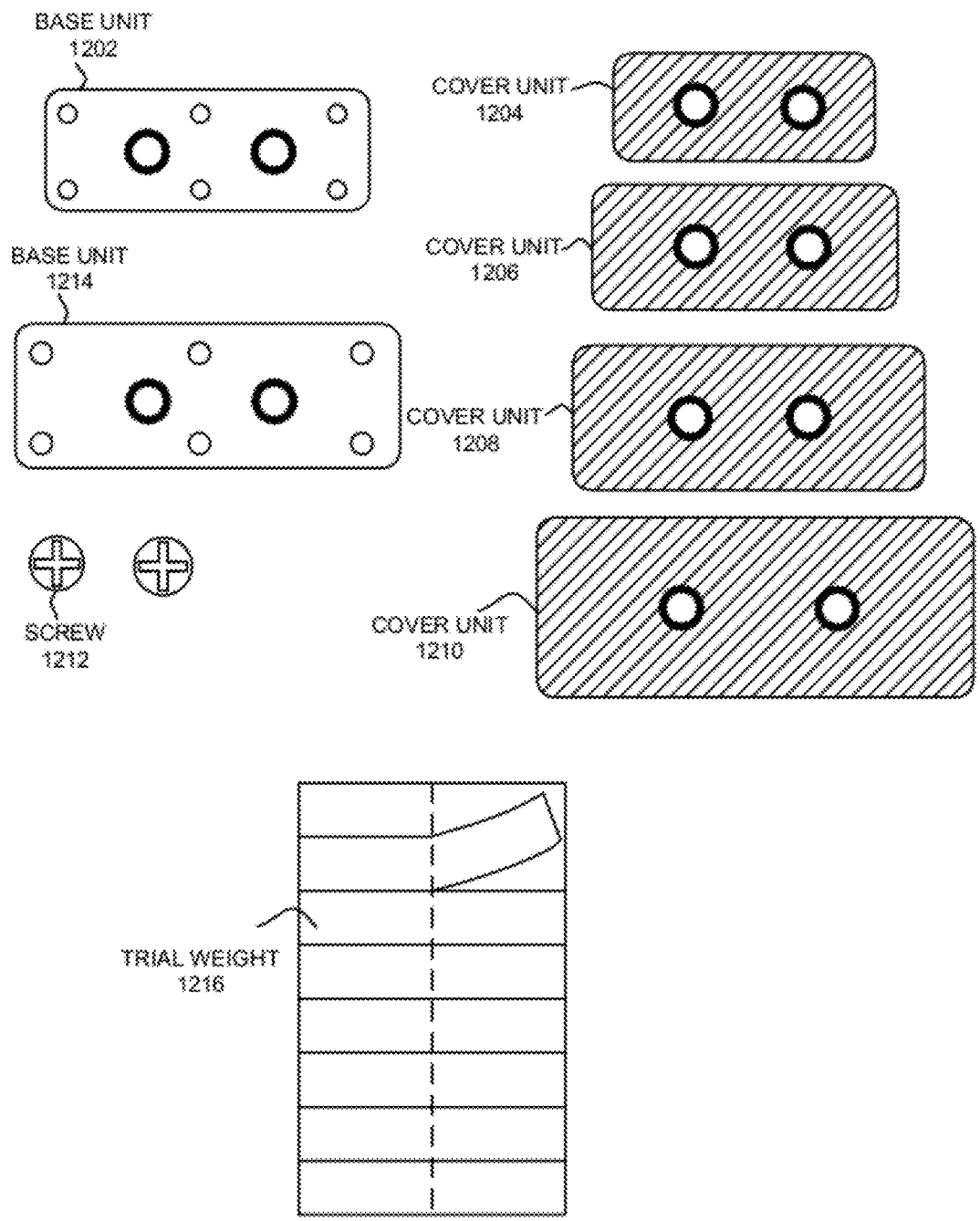
FIG. 12 shows an exemplary kit for use with a weighted eyelid closure device in accordance with an embodiment

FIG. 12 shows an exemplary kit for use with a weighted eyelid closure device in accordance with an embodiment. In accordance with an embodiment, the weighted eyelid closure device can be provided to surgeons and hospitals in kits. Each kit can contain a base unit 1202, including various cover units 1204, 1206, 1208 and 1210, and the required screws 1212 to attach the cover unit to the base unit. In an embodiment, each cover unit can be a different weight depending on the size and/or the material of the cover unit. In accordance with an embodiment, a plurality of different sizes (weight and length) of the base unit can be provided as part of the kit, and the surgeon or a fitting specialist can select from the kit the particular size of base unit (e.g., in an embodiment, base unit 1202, or the larger base unit 1214 can be selected) most suitable for the patient's need.

In accordance with an embodiment, the kit can also include various trial weights 1216 that are used to determine the desired weight of a device required for optimum closure of the eyelid. The trial weights are not implanted within the patient's eyelid, but are instead temporarily secured to the exterior of the eyelid. The trial weights are used to determine the appropriate weight of a device required for optimum closure of the eyelid by selecting one of the weights, temporarily affixing the weight to the exterior of the eyelid, and observing the position of the eyelid when the patient looks up and down and blinks. In an embodiment, the trial weight can be affixed to the exterior of the eyelid using an adhesive strip, although other adhesive means may be used to affix the device to the eyelid. The trial weight is then removed and, if necessary, a trial weight having a higher or lower weight is secured to the eyelid.

The foregoing description of the present invention has been provided for the purposes of illustration and description. It is not intended to be exhaustive or to limit the invention to the precise forms disclosed. Many modifications and variations will be apparent to the practitioner skilled in the art.

In particular, while various dimensions, numbers, and positions of suture and thread holes, loads and other features have been provided above, in accordance with other embodiments different dimensions, numbers, and positions can be used.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A weighted eyelid closure device, which can be implanted within a patient's eyelid to treat lagopthalmos, comprising:
   a base unit, formed in an elongated concave shape, and having obverse and reverse faces, and edges associated therewith,
      wherein the base unit is sized so that it can be implanted within the interior of a patient's eyelid, and
      wherein the concave shape approximately matches that of the eyelid or eye;
   a plurality of suture holes, distributed within or around the faces or edges of the base unit, which allow the base unit to be permanently attached to the interior of the eyelid;
   a load, positioned within or attached to the base unit, which can be removed or replaced from the base unit or otherwise adjusted, to adjust the total weight of the base unit and the load together; and
   wherein the base unit can be initially implanted within the patient's eyelid so that, at a subsequent time, the load can be adjusted, without removing the base unit, to treat lagopthalmos.

2. The weighted eyelid closure device of claim 1, wherein the base unit includes a repository adapted to receive a load by injecting the load into the repository, and wherein the weighted eyelid closure device's weight is adjusted by adding or removing said load from the repository.

3. The weighted eyelid closure device of claim 2, wherein the load includes a mixture of a first material, and a second material of a lower or equal atomic weight than the first material, and wherein the weighted eyelid closure device's weight is adjusted by adding or removing said mixture from the repository.

4. The weighed eyelid closure device of claim 3, wherein the device can be made to have different weights according to a process of:
   selecting a desired total volume of the device;
   selecting a plurality of desired total weights of the device; and
   altering the ratio between the first material and the second material, to adjust the total weight of the device to match the desired total weights, while maintaining the total volume substantially the same.

5. The weighted eyelid closure device of claim 1, wherein the base unit includes a pocket adapted to receive a load, and wherein the load is placed into or removed from the pocket to adjust the weighted eyelid closure's weight.

6. The weighted eyelid closure device of claim 1, wherein the base unit is made of tantalum and covered in a material with a color that blends with the color of the patient's eyelid.

7. The weighed eyelid closure device of claim 1, wherein said load includes a plurality of cover units each capable of being fastened to or removed from the base unit, wherein the weighted eyelid closure device's weight is adjusted by fastening or removing one the plurality of cover units form the base unit.

8. The weighted eyelid closure device of claim 7, wherein the plurality of cover units include a thread channel to which suture used in implanting the base unit within the eyelid lies in when the cover unit is fastened to the base.

9. The weighted eyelid closure device of claim 1, including a weight control disc as part of the base unit, the weight control disc providing an adjustable weight for the weighted eyelid closure device; and
   wherein the weight of the weighted eyelid closure device is adjusted by removing portions of said weight control disc.

10. The weighted eyelid closure device of claim 9, wherein the weight control disc is separated into a plurality of pieces, and wherein the weight of the weighted eyelid closure device is adjusted by removing one or more of the plurality of pieces.

11. The weighted eyelid closure device of claim 1, further including:
   a plurality of trial weights each having a different weight, said plurality of trial weights adapted to adhere to an exterior of an eyelid to determine a weight that closes the patient's eyelid, whereby said trial weights are used to determine the weight of the load positioned within or attached to said base unit.

12. A method for implanting a weighted eyelid closure device within a patient's eyelid to treat lagopthalmos, said method comprising the steps of:
   selecting a base unit, said base unit formed in an elongated concave shape, and having obverse and reverse faces, and edges associated therewith,
      wherein the base unit is sized so that it can be implanted within the interior of a patient's eyelid, and
      wherein the concave shape approximately matches that of the eyelid or eye;
   selecting a load, positioned within or attached to the base unit, which can be removed or replaced from the base unit or otherwise adjusted, to adjust the total weight of the base unit and the load together; and
   implanting the base unit in the patient's eyelid using a plurality of suture holes, said suture holes distributed within or around the faces or edges of the base unit, wherein the plurality of holes receive sutures which allow the base unit to be permanently attached to the interior of the eyelid.

13. The method of claim 12, further comprising:

adjusting, at a subsequent time, the load without removing the base unit, to treat lagopthalmos.

14. The method of claim 12, further comprising:

selecting an implanted weighted eyelid closure device that includes a base unit having a repository capable of receiving a load;

injecting the load into the repository; and wherein the base unit's total weight is adjusted by adding or removing said load.

15. The method of claim 12, further comprising:

adjusting the base unit's total weight by removing the load from the pocket and adding a new load to a pocket located in the base unit.

16. The method of claim 12, further comprising:

selecting an implanted weighted eyelid closure device that includes a base unit capable of being fastened to the load, which load includes one of a plurality of cover units; and adjusting the base unit's total weight by fastening one of the plurality of cover units to the base unit.

* * * * *